March 22, 1960 E. S. BOERNER Plant Pat. 1,923
CHRYSANTHEMUM PLANT
Filed June 30, 1959
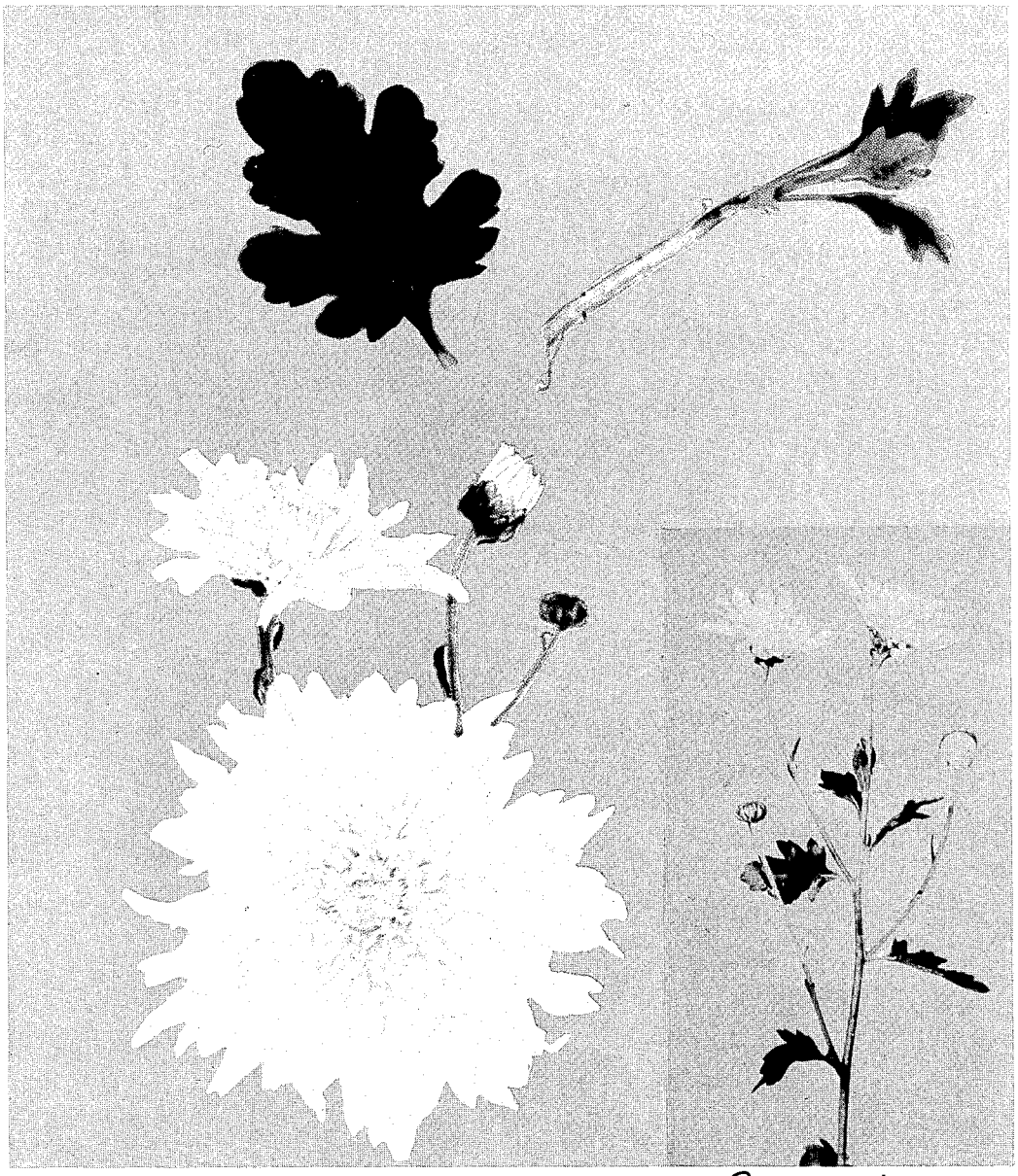
Inventor,
E. S. Boerner
By: Robb & Robb
Attorneys United States Patent Office Plant Pat. 1,923
Patented Mar. 22, 1960

1,923

CHRYSANTHEMUM PLANT

Eugene S. Boerner, Newark, N.Y., assignor to Jackson & Perkins Company, Newark, N.Y., a corporation of New York Application June 30, 1959, Serial No. 824,144

1 Claim. (Cl. 47—60)

The present invention relates to a new and distinct variety of chrysanthemum plant of the decorative type, which was originated by me by crossing an unnamed and unpatented White-flowered seedling of "Meadowlark" (Plant Patent No. 1,305) × "Thrush" (Plant Patent No. 1,168) with the variety "Orchard Oriole" (Plant Patent No. 1,461).

The primary objective of this breeding was to produce a new and improved chrysanthemum variety having the sturdy and vigorous plant habits of the parent variety "Orchard Oriole," combined with a flower size and color corresponding to the unnamed seedling parent originated from "Meadowlark" × "Thrush." This objective was fully achieved, along with other desirable improvements, as evidenced by the following characteristics which are outstanding in the new variety and which distinguish it from its parents, as well as from all other varieties of which I am aware:

(1) A sturdy and vigorous plant habit;
(2) Good hardiness;
(3) Large size of the flower;
(4) Full form of the flower; and
(5) A White general color tonality of the flower.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black-and-white, as illustrative of the form and habit of growth of the plant.

The following is a detailed description of the new variety, with color terminology in accordance with Ridgway's Color Standards and Nomenclature, as based upon observations made from specimens grown outdoors at Newark, New York, in the early afternoon near the middle of September:

Parentage: Seedling.
*Seed parent.*—An unnamed White-flowered seedling of "Meadowlark" × "Thrush."
*Pollen parent.*—"Orchard Oriole."

Classification: Decorative.
Growth: Medium height; full.
Cold resistance: The plant is winter hardy in northern New York; flowers show slight frost burn from early frosts.
Blooming period: In the Newark, New York climatic area, average date of start of bloom is late September, with bloom continuing until frost.

*Flower*

(Observations made from specimens grown outdoors at Newark, New York, in the early afternoon near the middle of September.)

Bud:
*Color.*—When sepals first divide—White, Plate 53, lightly overcast with Barium Yellow, Plate 16 on the edge of the petals. When petals begin to unfurl—White, Plate 53, with lower half of petals lightly overcast with Amber Yellow, Plate 16. When half-blown: inside of petals—White, Plate 53, lightly overcast with Strontium Yellow, Plate 16; outside of petals—White, Plate 53, with lower half of petals lightly overcast with Citron Yellow, Plate 16.
*Peduncle.* — Color — Rainette Green, Plate 31. Strength—strong.

Bloom:
*Size.*—5 inches.
*Stem.*—Medium strength.
*Form.*—Decorative.
*Petalage.*—Double.
*Color.*—Center of flower—White, Plate 53, lightly overcast with Mustard Yellow, Plate 16. Outer petals—White, Plate 53. Base of petals—Pale Greenish Yellow, Plate 5. Inside of petals—White, Plate 53. Reverse of petals—White, Plate 53.
*Petals.*—Texture—thick. Form—oval.
*Fragrance.*—Characteristic chrysanthemum.

*Plant*

Form: Low; compact.
Growth: Free; sturdy; vigorous.
Foliage:
*Size.*—Medium.
*Quantity.*—Normal.
*Color.*—Upper side—Elm Green, Plate 17. Under side—Light Elm Green, Plate 17.
*Texture.*—Leathery.

I claim:

A new and distinct variety of chrysanthemum plant of the decorative type, substantially as herein shown and described, characterized particularly as to novelty by the unique combination of a sturdy and vigorous plant habit, good hardness, large size and full form of the flowers, and a distinctive White general color tonality of the flowers.

No references cited.